US011389518B2

(12) United States Patent
Browning et al.

(10) Patent No.: US 11,389,518 B2
(45) Date of Patent: Jul. 19, 2022

(54) *MYCOPLASMA BOVIS* COMPOSITIONS (71) Applicants: Zoetis Services LLC, Parsippany, NJ (US); University of Melbourne, Carlton (AU)

(72) Inventors: Glenn Francis Browning, Parkville (AU); Philip Francis Markham, Parkville (AU); Marc Serge Marenda, Parkville (AU); Fred H. Weber, Kalamazoo, MI (US); Suman Mahan, Kalamazoo, MI (US)

(73) Assignees: Zoetis Services LLC, Parsippany, NJ (US); University of Melbourne

(*) Notice: Subject to any disclaimer, the term of this patent is extended or adjusted under 35 U.S.C. 154(b) by 100 days.

(21) Appl. No.: 15/751,293

(22) PCT Filed: Aug. 11, 2016

(86) PCT No.: PCT/US2016/046572
§ 371 (c)(1),
(2) Date: Feb. 8, 2018

(87) PCT Pub. No.: WO2017/030901
PCT Pub. Date: Feb. 23, 2017

(65) Prior Publication Data
US 2019/0255166 A1    Aug. 22, 2019

Related U.S. Application Data (60) Provisional application No. 62/205,125, filed on Aug. 14, 2015.

(51) Int. Cl.
*A61K 39/02* (2006.01)
*C12N 1/20* (2006.01)
*A61K 39/00* (2006.01)

(52) U.S. Cl.
CPC ............ *A61K 39/0241* (2013.01); *C12N 1/20* (2013.01); *A61K 2039/521* (2013.01); *A61K 2039/522* (2013.01); *A61K 2039/552* (2013.01)

(58) Field of Classification Search
None
See application file for complete search history.

(56) References Cited

U.S. PATENT DOCUMENTS

| 6,207,646 | B1 | 3/2001 | Krieg et al. |
| 6,548,069 | B2* | 4/2003 | Hymas ............... A61K 39/0241 424/184.1 |
| 8,586,059 | B2 | 11/2013 | Rosenbusch et al. |
| 2002/0150593 | A1 | 10/2002 | Hymas et al. |
| 2004/0170652 | A1 | 9/2004 | Nliholas |
| 2005/0053627 | A1 | 3/2005 | Leonard et al. |
| 2009/0068231 | A1 | 3/2009 | Kumar et al. |
| 2009/0130148 | A1 | 5/2009 | Beck et al. |
| 2012/0093854 | A1 | 4/2012 | Beck et al. |

FOREIGN PATENT DOCUMENTS

| EP | 2421556 B1 | 2/2012 |
| WO | WO 92/19265 A1 | 11/1992 |
| WO | WO 98/17799 A1 | 4/1998 |
| WO | WO 99/43839 A1 | 9/1999 |
| WO | WO 2003/004052 A1 | 1/2003 |

OTHER PUBLICATIONS

Nicholas et al (Journal of Comparative Pathology, 140(2-3):85-96; 2009).*
Perez-Casal et al; Vaccine, 35:2902-2907, 2017.*
Pfutzner et al (Rev. sci. tech. Off. int. Epiz, 15(4):1477-1494, 1996).*
Nicholas, R. A. J. et al., 2009, "Vaccines for Mycoplasma diseases in Animals and Man", Journal of Comparative Pathology, vol. 140, pp. 85-96.
Li, Y. et al., 2011, The Complete Genome Sequence of Mycoplasma bovis Strain Hubei-1, PLOS One, vol. 6, e20999.
Nonomura, I. et al., 1982, "Temperature-Sensitive Mutant of Mycoplasma synoviae", Avian Diseases, vol. 26, pp. 763-775.
GenBank: Accession No. CP002513, Jan. 30, 2014, Mycoplasma bovis Hubei-1, complete genome https://www.ncbi.nlm.nih.gov/nuccore/CP002513.
PCT International Search Report, International Filing Date Aug. 11, 2016; International Application No. PCT/US2016/046572, dated Nov. 3, 2016.

* cited by examiner

*Primary Examiner* — Patricia Duffy
(74) *Attorney, Agent, or Firm* — Vyacheslav Vasilyev (57) ABSTRACT Disclosed herein are *Mycoplasma bovis* immunogenic compositions useful in raising an immune response in animals against *M. bovis*. Also disclosed herein are methods for generating a protective response against infections in mammals caused by *M. bovis*.

12 Claims, 1 Drawing Sheet

MYCOPLASMA BOVIS COMPOSITIONS

The present application is the United States National Stage (35 USC 371) of International Application PCT/US2016/046572, filed Aug. 11, 2016, and claims the benefit of U.S. Provisional Application No. 62/205,125, filed Aug. 14, 2015.

FIELD OF THE INVENTION

The present invention relates to *Mycoplasma bovis* immunogenic compositions. The present invention further relates to immunogenic compositions for use in raising an immune response in animals against *M. bovis*, and methods for generating a protective response against infections in mammals caused by *M. bovis*.

BACKGROUND OF THE INVENTION

*Mycoplasma bovis* causes multiple diseases in bovine herds around the world, including, for example, mastitis, pneumonia, arthritis, otitis, skin abscesses, infertility, abortion, or combinations thereof. In each form of the disease, mortality can occur. *M. bovis* is thus a significant concern to dairy and beef producers, and veterinarians world-wide. A variety of antibiotics have been developed and proposed as tools to mitigate the economic losses and mortality produced by this pathogen. Preventing the disease through the application of a safe and effective vaccine offers significant advantages to antibiotic therapy through enhancing animal welfare, improving producer economics, and supporting the judicious use of antibiotics. Vaccines containing inactivated (e.g., killed) *M. bovis* have been developed. However, killed vaccines typically present long delays in the initiation of a protective response, may require more than one dose, and in some cases, may require adjuvants that are not suitable in certain applications.

Live-attenuated, or modified-live, vaccines are advantageous in that they can lead to the development of a more rapid immune response, are often effective when administered in a single dose, and are generally less expensive to produce. Thus, there is a need for improved *M. bovis* vaccines, including live-attenuated ones.

SUMMARY OF THE INVENTION

Applicants have surprisingly identified immunogenic compositions useful for generating a protective immune response against *Mycoplasma bovis* infection in mammals. They can additionally be combined with an adjuvant. Said compositions can also be combined with additional antigens, yielding multivalent compositions for combating multiple infections in mammals.

One embodiment of the invention provides an immunogenic composition comprising an attenuated *Mycoplasma bovis* strain, wherein said strain is deposited with the American Type Culture Collection under accession number PTA-122167.

Another embodiment provides an immunogenic composition comprising a chemically-attenuated *Mycoplasma bovis* strain which, in comparison to a parent strain, has one or more mutations in one or more of the proteins nitroreductase, histidine acid phosphatase, excinuclease ABC subunit B, DNA polymerase III subunit beta, and ATP synthase F1 subunit delta.

Another embodiment provides an immunogenic composition comprising a *Mycoplasma bovis* strain, wherein said strain is PTA-122167, further wherein said strain has been reverse engineered to contain one or more of any of the original nucleotides found in reference *M. bovis* strain, 3683 #22/3/12, at positions 115273, 194478, 194484, 194525, 194724, 204966, 207629, 262327, 271487, 271661, 271666, 272086, 272133, 309463, 310075, 310078, 310086, 310090, 311988, 334184, 358013, 365101, 365188, 397010, 397901, 399129, 410247, 410253, 410334, 410514, 410733, 414666, 453388, 468457, 502577, 502678, 502963, 543859, 560986, 632309, 632366, 632612, 633994, 686074, 687874, 687915, 696348, 729874, 730046, 761587, 761663, 761810, 761815, 765176, 765328, and 765403 thereof, according to the nucleotide numbering of the reference genome of *M. bovis* strain, Hubei-1.

Another embodiment provides an immunogenic composition comprising the attenuated *M. bovis* strain of the previous embodiment, wherein said *M. bovis* strain is inactivated.

Another embodiment provides the immunogenic composition of any of the previous embodiments, and additionally an adjuvant.

Another embodiment provides the immunogenic composition of any of the previous embodiments, further comprising at least one additional antigen.

Another embodiment provides the immunogenic composition of the previous embodiment, wherein the additional antigen is selected from the group consisting of a virus, a bacterium, a fungus and a parasite.

Another embodiment provides an immunogenic composition of any of the previous embodiments, wherein said composition is formulated for administration by a route selected from the group consisting of intramuscular, subcutaneous, intranasal, intratracheal, oral and aerosol.

Another embodiment provides a method for preventing disease caused by *M. bovis* in a bovine animal, comprising administering to the animal an immunizing amount of the immunogenic composition of any of the previous embodiments.

Another embodiment provides a method for preventing diseases caused by *M. bovis* and another infectious agent of a bovine animal, comprising administering to the animal an immunizing amount of the immunogenic composition of any of the previous embodiments, and an additional antigen.

Another embodiment provides the use of an attenuated *M. bovis* strain, or an inactivated attenuated *M. bovis* strain, in the manufacture of a medicament for preventing disease caused by *M. bovis* in a bovine animal.

Another embodiment provides a *Mycoplasma bovis* vaccine, generated by the steps comprising: (A) obtaining a culture of *M. bovis* deposited with the ATCC as PTA-122167; (B) further passaging said culture of *M. bovis* at least once; (C) isolating a clone from said passaged culture; and (D) formulating said clone with a carrier or excipient, and optionally an adjuvant.

Another embodiment provides the vaccine of the previous embodiment, wherein the clone obtained from the passaged culture is more attenuated than PTA-122167.

Another embodiment provides a method of providing a *Mycoplasma bovis* vaccine, wherein said vaccine is generated by the steps comprising: (A) obtaining a culture of *M. bovis* deposited with the ATCC as PTA-122167; (B) further passaging said culture of *M. bovis* at least once; (C) isolating a clone from said passaged culture; and (D) formulating said clone with a carrier or excipient, and optionally an adjuvant.

Another embodiment provides a method of mutagenizing a parental strain of *M. bovis*, wherein said method comprises subjecting said strain to a chemical mutagen, followed by selection of a progeny strain that remains viable after serial passaging in vitro.

Another embodiment provides a method of mutagenizing a parental strain of *M. bovis*, wherein the parental strain is *Mycoplasma bovis* strain 3683.

Another embodiment provides a method of mutagenizing a parental strain of *M. bovis*, wherein the progeny strain is deposited with the American Type Culture Collection under accession number PTA-122167.

Another embodiment provides a method of mutagenizing a parental strain of *M. bovis*, wherein said method comprises subjecting said strain to a chemical mutagen, followed by selection of a progeny strain that remains viable after serial passaging in vitro, wherein the progeny strain contains one or more of any of the original nucleotides at positions 115273, 194478, 194484, 194525, 194724, 204966, 207629, 262327, 271487, 271661, 271666, 272086, 272133, 309463, 310075, 310078, 310086, 310090, 311988, 334184, 358013, 365101, 365188, 397010, 397901, 399129, 410247, 410253, 410334, 410514, 410733, 414666, 453388, 468457, 502577, 502678, 502963, 543859, 560986, 632309, 632366, 632612, 633994, 686074, 687874, 687915, 696348, 729874, 730046, 761587, 761663, 761810, 761815, 765176, 765328, and 765403, according to the nucleotide numbering of the reference genome of *M. bovis* strain, Hubei-1.

DETAILED DESCRIPTION

All publications, patent applications, patents, and other references mentioned herein are incorporated by reference in their entirety.

Unless otherwise defined herein, scientific and technical terms used in connection with the present embodiments shall have the meanings that are commonly understood by those of ordinary skill in the art. Further, unless otherwise required by context, singular terms shall include pluralities, and plural terms shall include the singular.

The term "adjuvant", as used herein, means a pharmacological or immunological agent that modifies the effect of other agents, such as a drug or immunogenic composition. Adjuvants are often included in immunogenic compositions to enhance the recipient's immune response to a supplied antigen. See below for a further description of adjuvants.

The terms "antibody" or "antibodies", as used herein, mean an immunoglobulin molecule able to bind to an antigen by means of recognition of an epitope.

Immunoglobulins are serum proteins composed of "light" and "heavy" polypeptide chains, which have "constant" and "variable" regions, and are divided into classes (e.g., IgA, IgD, IgE, IgG, and IgM) based on the composition of the constant regions. An antibody that is "specific" for a given antigen indicates that the variable regions of the antibody recognize and bind a particular antigen exclusively. Antibodies can be a polyclonal mixture, or monoclonal. They can be intact immunoglobulins derived from natural or recombinant sources, or can be immunoreactive portions of intact immunoglobulins. Antibodies can exist in a variety of forms, including Fv, Fab', F(ab')2, Fc, as well as single chain. An antibody can be converted to an antigen-binding protein, which includes, but is not limited to, antibody fragments. As used herein, the term "antigen binding protein", "antibody" and the like, which may be used interchangeably, refer to a polypeptide or polypeptides, or fragment(s) thereof, comprising an antigen binding site. The term "antigen binding protein" or "antibody" preferably refers to monoclonal antibodies and fragments thereof, and immunologic-binding equivalents thereof that can bind to a particular protein and fragments thereof. As used herein, the term encompasses not only intact polyclonal or monoclonal antibodies, but also fragments thereof. For the purposes of the present invention, "antibody" and "antigen binding protein" also includes antibody fragments, unless otherwise stated. Exemplary antibody fragments include Fab, Fab', F(ab')2, Fv, scFv, Fd, dAb, diabodies, their antigen-recognizing fragments, small modular immunopharmaceuticals (SMIPs) nanobodies and the like, all recognized by one of skill in the art to be an antigen binding protein or antibody fragment, and any of above-mentioned fragments and their chemically or genetically manipulated counterparts, as well as other antibody fragments and mutants thereof, fusion proteins comprising an antibody portion, and any other modified configuration of the immunoglobulin molecule that comprises an antigen recognition site. Antibodies and antigen binding proteins can be made, for example, via traditional hybridoma techniques (Kohler et al., Nature 256:495-499 (1975)), recombinant DNA methods (U.S. Pat. No. 4,816,567), or phage display techniques using antibody libraries (Clackson et al., Nature 352:624-628 (1991); Marks et al., J. Mol. Biol. 222:581-597 (1991)). For various other antibody production techniques, see Antibodies: A Laboratory Manual, eds. Harlow et al., Cold Spring Harbor Laboratory, 1988 as well as other techniques that are well known to those skilled in the art.

"Antigen", as used herein, means a molecule that contains one or more epitopes (linear, conformational or both), that upon exposure to a subject, will induce an immune response that is specific for that antigen. An epitope is the specific site of the antigen which binds to a T-cell receptor or specific B-cell antibody, and typically comprises about 3 to about 20 amino acid residues. The term "antigen" can also refer to subunit antigens—antigens separate and discrete from a whole organism with which the antigen is associated in nature—as well as killed, attenuated or inactivated bacteria, viruses, fungi, parasites or other microbes. The term "antigen" also refers to antibodies, such as anti-idiotype antibodies or fragments thereof, and to synthetic peptide mimotopes that can mimic an antigen or antigenic determinant (epitope). The term "antigen" also refers to an oligonucleotide or polynucleotide that expresses an antigen or antigenic determinant in vivo, such as in DNA immunization applications. An "antigen", as used herein, is a molecule or a portion of a molecule capable of being specifically bound by an antibody or antigen binding protein. In particular, an antibody, or antigen binding protein, will bind to epitopes of the antigen. An epitope, as used herein, refers to the antigenic determinant recognized by the hypervariable region, or Complementarity Determining Region (CDR), of the variable region of an antibody or antigen binding to protein.

The term "animal", as used herein, means any animal that is susceptible to infection by *Mycoplasma bovis*, both domesticated and wild. Preferably, "animal", as used herein, refers to a bovine.

The term "attenuated", as used herein, refers to a strain of a microorganism whose pathogenicity has been reduced so that it will generally initiate an immune response but without producing disease. An attenuated strain is less virulent than the parental strain from which it was derived. Attenuated microorganisms can be screened in vitro or in vivo to confirm that they are less pathogenic than its parental strain. Conventional means are used to introduce attenuating mutations, such as in vitro passaging, as well as chemical mutagenesis. An alternative means of attenuating comprises making pre-determined mutations using site-directed mutagenesis, where one or more mutations may be introduced. The term "more attenuated", as used herein, refers to a strain which has been further modified beyond the attenuated strain from which it was derived. This further attenuation can be achieved through additional in vitro passaging, or additional rounds of chemical or site-directed mutagenesis. To be useful as a live vaccine, any attenuated organism must nonetheless cause the host immune system to initiate an effective immune response, which may require some growth of the organism.

The terms "bacteria", "bacterial species", "bacterium", and the like, as used herein, mean a large domain of prokaryotic microorganisms.

The term "bovine", as used herein, means a diverse group of medium- to large-sized ungulates, generally having cloven hoofs, and at least one of the sexes having true horns. Bovines include, but are not limited to, domestic cattle, bison, African buffalo, water buffalo, yak, and four-horned or spiral-horned antelope.

The term "chemical mutagenesis", as used herein, means the use of a compound that increases the frequency of some types of mutation(s) occurring above the natural background level. The compounds used can vary in their potency, since they can differ in their ability to enter a cell, in the extent of their reactivity with nucleic acids, in their general toxicity, and in the likelihood that the type of chemical change they introduce into the nucleic acid will be corrected by a endogenous repair system.

The term "immunogenic composition" or "immunizing amount", as used herein, means a composition that generates an effective immune response (i.e., has effective and/or at least partially protecting immunogenic activity) when administered alone, or with a pharmaceutically-acceptable carrier, to an animal. The immune response can be a cellular immune response mediated primarily by cytotoxic T-cells, or a humoral immune response mediated primarily by helper T-cells, which in turn activate B-cells, leading to antibody production. In addition, specific T-lymphocytes or antibodies can be generated to allow for the future protection of an immunized host.

The term "isolated", as used herein, means that the referenced material is removed from some of the components of the environment in which it is normally found. Thus, an isolated biological material can be free of some cellular components, i.e., components of the cells in which the material is found or produced. In the case of nucleic acid molecules, an isolated nucleic acid includes, for example, a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes located upstream or downstream of the nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified. An "isolated" or "purified" polypeptide or polynucleotide, e.g., an "isolated polypeptide," or an "isolated to polynucleotide", is purified to a state beyond that in which it exists in nature. For example, the "isolated" or "purified" polypeptide or polynucleotide, can be substantially free of cellular material or other contaminating proteins from the cell or tissue source from which the protein or polynucleotide is derived, or substantially free from chemical precursors or other chemicals when chemically synthesized. The preparation of antigen binding protein having less than about 50% of non-antigen binding protein (also referred to herein as a "contaminating protein"), or of chemical precursors, is considered to be "substantially free." 40%, 30%, 20%, 10% and more preferably 5% (by dry weight), of non-antigen binding protein, or of chemical precursors, is considered to be substantially free.

The term "medicament", as used herein, means an agent that promotes recovery from an infection, injury or ailment; a medicine.

The term "mutant", as used herein, means an individual or organism arising or resulting from an instance of mutation, which is a base-pair sequence change within the nucleic acid or chromosome of an organism, and results in the creation of a new character or trait not found in the wild-type individual or organism.

The term "parent" or "parental strain", as used herein, means the entity from which offspring, or progeny, are derived. The term "progeny", as used herein, means that produced by, or derived from, one or more parents or parental strains.

The terms "prevent", "preventing" or "prevention", and the like, as used herein, mean to inhibit the replication of a microorganism, to inhibit transmission of a microorganism, or to inhibit a microorganism from establishing itself in its host. These terms, and the like, can also mean to inhibit or block one or more signs or symptoms of infection.

The terms "reverse engineer" or "reverse mutagenize", as used herein, mean to reintroduce by genetic means (e.g. polymerase chain reaction, or PCR) the original nucleotide sequence occurring at a particular position(s) within a microorganism's genome, wherein that sequence had previously been changed.

The terms "serial passage" or "serial passaging", as used herein, mean a method for purifying an organism, preferably a microorganism, to obtain a clonally pure population. The terms can also refer to a technique for attenuating, or weakening, the virulence of an organism, preferably a microorganism.

The term "therapeutically effective amount" (or "effective amount"), as used herein, means an amount of an active ingredient, e.g., an agent according to the invention, with or without an adjuvant, as appropriate under the circumstances, provided in a single or multiple doses as appropriate, sufficient to effect beneficial or desired results when administered to a subject or patient. An effective amount can be administered in one or more administrations, applications or dosages. A therapeutically effective amount of a composition according to the invention may be readily determined by one of ordinary skill in the art, and provides a measurable benefit to a patient, such as protecting the animal from subsequent challenge with a similar pathogen.

As used herein, the terms "therapeutic" or "treatment" encompass the full spectrum of treatments for a disease or disorder. By way of example, a "therapeutic" agent of the invention may act in a manner, or a treatment may result in an effect, that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

The term "veterinarily-acceptable carrier", as used herein, refers to substances which are, within the scope of sound medical judgment, suitable for use in contact with the tissues of animals, without undue toxicity, irritation, allergic response, and the like, commensurate with a reasonable benefit-to-risk ratio, and effective for their intended use.

The following description is provided to aid those skilled in the art in practicing the present invention. Even so, this description should not be construed to unduly limit the present invention, as modifications and variations in the embodiments discussed herein can be made by those of ordinary skill in the art, without departing from the spirit or scope of the present inventive discovery.

Bacteria: Immunogenic Compositions

In certain embodiments of the present invention, a *Mycoplasma bovis* strain from a bovine has been attenuated, as well as characterized. An isolate of said *M. bovis* strain was deposited with the American Type Culture Collection ("ATCC"), Manassas, Va., USA, on May 12, 2015, and has been assigned accession number, PTA-122167.

Immunogenic compositions of the present invention can be attenuated or inactivated prior to use in an immunogenic composition. Methods of attenuation and inactivation are well known to those skilled in the art. Methods for attenuation include, but are not limited to, serial passage in cell culture, ultraviolet irradiation, and chemical mutagenesis. A large number of chemical mutagens may interact directly with DNA. However, many chemicals, such as aromatic amines and benzene are not necessarily mutagenic by themselves, but through metabolic processes in cells, they produce mutagenic compounds. Chemical mutagens can also include reactive oxygen species (ROS). These may include superoxide, hydroxyl radicals and hydrogen peroxide. A large number of these highly reactive species are generated by normal cellular processes, for example as by-products of mitochondrial electron transport, or lipid peroxidation. A number of other chemical mutagens may also generate these ROS. These ROS may result in the production of various base adducts, as well as DNA strand breaks and crosslinks. Chemical mutagens can also include deaminating agents, for example nitrous acid, which can cause transition mutations by converting cytosine to uracil. Polycyclic aromatic hydrocarbon (PAH), is also a chemical mutagen. When activated, it can bind to DNA and form adducts. Chemical mutagens can also include alkylating agents, such as ethylnitrosourea. These compounds transfer methyl or ethyl group to bases or the backbone phosphate groups. Guanine, when alkylated, may be mispaired with thymine. Some of these alkylating agents may cause DNA crosslinking and breakages. Nitrosamines are an important group of mutagens, such as can be found in tobacco. Methylnitronitrosoguanidine (MNNG, MNG, or NTG) is an alkylating agent which acts by adding alkyl groups to the $O^6$ of guanine and $O^4$ of thymine, which can lead to transition mutations between GC and AT. These changes do not cause a heavy distortion in the double helix of DNA, and thus are hard to detect by the DNA mismatch repair system. Other alkylating agents can also include mustard gas and vinyl chloride.

Methods for inactivation include, but are not limited to, treatment with formalin, betapropriolactone (BPL) or binary ethyleneimine (BEI), or other methods known to those skilled in the art. Inactivation by formalin can be performed by mixing the bacterial suspension with 37% formaldehyde, to a final formaldehyde concentration of 0.05%. The bacteria-formaldehyde mixture is stirred constantly for approximately 24 hours at room temperature. The inactivated bacterial mixture is then tested for residual live bacteria by assaying for growth in culture media. Inactivation by BEI can be performed by mixing the bacterial suspension with 0.1 M BEI (2-bromo-ethylamine in 0.175 N NaOH), to a final BEI concentration of 1 mM. The bacteria-BEI mixture is stirred constantly for approximately 48 hours at room temperature, followed by the addition of 1.0 M sodium thiosulfate to a final concentration of 0.1 mM. Mixing is continued for an additional two hours. The inactivated bacterial mixture is tested for residual live bacteria by assaying for growth in culture media.

Effective (i.e. protecting) Immunogenic compositions of the present invention can include one or more veterinarily-acceptable carriers, such as any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others known to those skilled in the art. Stabilizers include albumin, among others known to the skilled artisan. Preservatives include merthiolate, among others known to the skilled artisan.

Effective immunogenic compositions of the present invention can include one or more adjuvants. Adjuvants include, but are not limited to, the RIBI adjuvant system (Ribi Inc.; Hamilton, Mont.), alum, aluminum hydroxide gel, oil-in water emulsions, water-in-oil emulsions such as, e.g., Freund's complete and incomplete adjuvants, Block co-polymer (CytRx; Atlanta, Ga.), SAF-M (Chiron; Emeryville, Calif.), AMPHIGEN® adjuvant, saponin, Quil A, QS-21 (Cambridge Biotech Inc.; Cambridge, Mass.), GPI-0100 (Galenica Pharmaceuticals, Inc.; Birmingham, Ala.) or other saponin fractions, monophosphoryl lipid A, Avridine lipid-amine adjuvant, heat-labile enterotoxin from *Escherichia coli* (recombinant or otherwise), cholera toxin, or muramyl dipeptide, among many others known to those skilled in the art.

The amounts and concentrations of adjuvants and additives useful in the context of the present invention can readily be determined by the skilled artisan, and appropriate amounts of each such substance are generally known or can be readily determined. In one embodiment, the present invention contemplates immunogenic compositions comprising from about 50 µg to about 2000 µg of adjuvant. In another embodiment, adjuvant is included in an amount from about 100 µg to about 1500 µg, or from about 250 µg to about 1000 µg, or from about 350 µg to about 750 µg. In another embodiment, adjuvant is included in an amount of about 500 µg/2 ml dose of the immunogenic composition. Generally, vaccines of the present invention are provided as 1-2 ML doses.

A number of cytokines or lymphokines have been shown to have immune modulating activity, and thus may be used as adjuvants, including, but not limited to, the interleukins 1-α, 1-13, 2, 4, 5, 6, 7, 8, 10, 12 (see, e.g., U.S. Pat. No. 5,723,127), 13, 14, 15, 16, 17 and 18 (and its mutant forms), the interferons-α, β and γ, granulocyte-macrophage colony stimulating factor (see, e.g., U.S. Pat. No. 5,078,996 and ATCC Accession Number 39900), macrophage colony stimulating factor, granulocyte colony stimulating factor, GSF, and the tumor necrosis factors α and β. Still other adjuvants useful in this invention include a chemokine, including without limitation, MCP-1, MIP-1α, MIP-1β, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE). See, also International Patent Publication Nos. WO98/17799 and WO99/43839, incorporated herein by reference.

Suitable adjuvants used to enhance an immune response also include, without limitation, MPL™ (3-O-deacylated monophosphoryl lipid A; Corixa, Hamilton, Mont.), which is described in U.S. Pat. No. 4,912,094, which is hereby incorporated by reference. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino] ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form or as a stable emulsion.

Still other adjuvants include mineral oil and water emulsions, aluminum salts (alum), such as aluminum hydroxide, aluminum phosphate, etc., Amphigen, Avridine, L121/squalene, D-lactide-polylactide/glycoside, pluronic polyols, muramyl dipeptide, killed *Bordetella*, saponins, such as Stimulon™ QS-21 (Antigenics, Framingham, Mass.), described in U.S. Pat. No. 5,057,540, which is hereby incorporated by reference, and particles generated therefrom such as ISCOMS (immunostimulating complexes), *Mycobacterium tuberculosis*, bacterial lipopolysaccharides, synthetic polynucleotides such as oligonucleotides containing a CpG motif (U.S. Pat. No. 6,207,646, which is hereby incorporated by reference), a pertussis toxin (PT), or an *E. coli* heat-labile toxin (LT), particularly LT-K63, LT-R72, PT-K9/G129; see, e.g., International Patent Publication Nos. WO 93/13302 and WO 92/19265, incorporated herein by reference.

Also useful as adjuvants are cholera toxins (CT) and mutants thereof, including those described in published International Patent Application number WO 00/18434 (wherein the glutamic acid at amino acid position 29 is replaced by another amino acid, other than aspartic acid, preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36). Said CT toxins or mutant can be included in the immunogenic compositions either as separate entities, or as fusion partners for the neurotoxic peptides of the present invention.

The immunogenic compositions of the invention can also include surface-active substances. Suitable surface-active substances include, without limitation, quinone analogs, hexadecylamine, octadecylamine, octadecyl amino acid esters, lysolecithin, dimethyl-dioctadecylammonium bromide, methoxyhexadecylgylcerol, and pluronic polyols; polyamines, e.g., pyran, dextransulfate, poly IC, carbopol; peptides, e.g., muramyl peptide and dipeptide, dimethylglycine, tuftsin; oil emulsions; and mineral gels, e.g., aluminum phosphate, etc., and immune-stimulating complexes (ISCOMS).

All the aforementioned adjuvants and additional substances can be used in amounts readily subject to determination by those skilled in the art.

The immunogenic compositions of the invention can also include antibiotics. Such antibiotics include, but are not limited to, those from the classes of aminoglycosides, carbapenems, cephalosporins, glycopeptides, macrolides, penicillins, polypeptides, quinolones, sulfonamides, and tetracyclines. In one embodiment, the present invention contemplates immunogenic compositions comprising from about 1 µg/ml to about 60 µg/ml of antibiotic. In another embodiment, the immunogenic compositions comprise from about 5 µg/ml to about 55 µg/ml of antibiotic, or from about 10 µg/ml to about 50 µg/ml of antibiotic, or from about 15 µg/ml to about 45 µg/ml of antibiotic, or from about 20 µg/ml to about 40 µg/ml of antibiotic, or from about 25 µg/ml to about 35 µg/ml of antibiotic. In yet another embodiment, the immunogenic compositions comprise less than about 30 µg/ml of antibiotic.

Other additives can also be included in the immunogenic compositions of this invention, including preservatives, stabilizing ingredients, and the like. Suitable exemplary preservatives include chlorobutanol, potassium sorbate, sorbic acid, sulfur dioxide, propyl gallate, the parabens, ethyl vanillin, glycerin, phenol, and parachlorophenol. Suitable stabilizing ingredients that may be used include, for example, casamino acids, sucrose, gelatin, phenol red, N-Z amine, monopotassium diphosphate, lactose, lactalbumin hydrolysate, and dried milk. The immunogenic compositions may also be incorporated into liposomes for use as an immunogenic composition, and may also contain other additives suitable for the selected mode of administration of the composition. The composition may include other pharmaceutically-acceptable excipients for developing powder, liquid or suspension dosage forms. See, e.g., Remington: The Science and Practice of Pharmacy, Vol. 2, 19$^{th}$ edition (1995), e.g., Chapter 95 Aerosols; and International Patent Publication No. WO99/45966, the teachings of which are hereby incorporated by reference.

Immunogenic compositions of the invention can include other antigens. Antigens can be in the form of an inactivated whole or partial preparation of the microorganism, or in the form of antigenic molecules obtained by recombinant techniques or chemical synthesis. Other antigens appropriate for use in accordance with the present invention include, but are not limited to, those derived from pathogenic bacteria, such as *Haemophilus somnus, Haemophilus parasuis, Bordetella bronchiseptica, Bacillus anthracis, Actinobacillus pleuropneumonie, Pasteurella multocida, Mannhemia haemolytica, Mycoplasma bovis, Mycobactenum bovis, Mycobacterium paratuberculosis, Clostridial* spp., *Streptococcus uberis, Staphylococcus aureus, Erysipelothnx rhusopathiae, Chlamydia* spp., *Brucella* spp., *Vibrio* spp., *Salmonella enterica serovars* and *Leptospira* spp. Antigens can also be derived from pathogenic fungi, such as *Candida*, protozoa such as *Cryptosporidium parvum, Neospora canium, Toxoplasma gondii, Eimena* spp., *Babesia* spp., *Giardia* spp., or helminths such as *Ostertagia, Cooperia, Haemonchus*, and *Fasciola*. Additional antigens can include pathogenic viruses, such as bovine coronavirus, bovine rotavirus, bovine herpesviruses, bovine parainfluenza virus, bovine viral diarrhea virus, bovine adenovirus, bovine rhinovirus, bovine reovirus, bovine respiratory syncytial virus, bovine leukosis virus, rinderpest virus, foot and mouth disease virus, and rabies virus.

Forms, Dosages, Routes and Timing of Administration

Immunogenic compositions of the present invention can be administered to animals to induce an effective immune response against *M. bovis*. Accordingly, the present invention provides methods of stimulating an effective immune response against *M. bovis* by administering to an animal a therapeutically effective amount of an immunogenic composition of the present invention described herein.

Immunogenic compositions of the present invention can be made in various forms, depending upon the route of administration. For example, the immunogenic compositions can be made in the form of sterile aqueous solutions or dispersions suitable for injectable use, or made in lyophilized forms using freeze-drying techniques. Lyophilized immunogenic compositions are typically maintained at about 4° C., and can be reconstituted in a stabilizing solution, e.g., saline or HEPES, with or without adjuvant. Immunogenic compositions can also be made in the form of suspensions or emulsions.

These immunogenic compositions can contain additives suitable for administration via any conventional route of administration. The immunogenic compositions of the invention can be prepared for administration to subjects in the form of, for example, liquids, powders, aerosols, tablets, capsules, enteric-coated tablets or capsules, or suppositories. Thus, the immunogenic compositions may also include, but are not limited to, suspensions, solutions, emulsions in oily or aqueous vehicles, pastes, and implantable sustained-release or biodegradable formulations. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Other useful parenterally-administrable formulations include those which comprise the active ingredient in microcrystalline form, in a liposomal preparation, or as a component of a biodegradable polymer system. Compositions for sustained release or implantation may comprise pharmaceutically acceptable polymeric or hydrophobic materials, such as an emulsion, an ion exchange resin, a sparingly soluble polymer, or a sparingly soluble salt.

Immunogenic compositions of the present invention include a therapeutically effective amount of *M. bovis*. Purified bacteria can be used directly in an immunogenic composition, or can be further attenuated, or inactivated. Typically, an effective immunogenic composition contains between about $1\times10^2$ and about $1\times10^{12}$ bacterial particles, or between about $1\times10^3$ and about $1\times10^{11}$ bacterial particles, or between about $1\times10^4$ and about $1\times10^{10}$ bacterial particles, or between about $1\times10^5$ and about $1\times10^9$ bacterial particles, or preferably between about $1\times10^6$ and about $1\times10^8$ bacterial particles. The precise amount of a bacterium in an immunogenic composition effective to provide a protective effect can be determined by a skilled artisan.

Effective Immunogenic compositions generally comprise a veterinarily-acceptable carrier in a volume of between about 0.5 ml and about 5 ml. In another embodiment the volume of the carrier is between about 1 ml and about 4 ml, or between about 2 ml and about 3 ml. In another embodiment, the volume of the carrier is about 1 ml, or is about 2 ml, or is about 5 ml. Veterinarily-acceptable carriers suitable for use in immunogenic compositions can be any of those described herein.

Such carriers include, without limitation, water, saline, buffered saline, phosphate buffer, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-Hel, carbonic acid, tartaric acid, succinic acid, acetic acid, phthalic acid, Tris, trimethanmine hydrochloride, or phosphate buffers. Parenteral carriers can include sodium chloride solution, Ringer's dextrose, dextrose, trehalose, sucrose, lactated Ringer's, or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH, isotonicity, stability and other conventional characteristics, is within the skill of the art. See, e.g., texts such as Remington: The Science and Practice of Pharmacy, 20th ed., Lippincott Williams & Wilkins, pub., 2000; and The Handbook of Pharmaceutical Excipients, 4.sup.th edit., eds. R. C. Rowe et al, APhA Publications, 2003.

Those skilled in the art can readily determine whether a bacterium needs to be attenuated or inactivated before administration. In another embodiment of the present invention, *M. bovis* can be administered directly to an animal without additional attenuation. The amount of a bacterium that is therapeutically effective can vary depending on the particular bacterium used, the condition of the animal and/or the degree of infection, and can be determined by a skilled artisan.

In accordance with the methods of the present invention, a single dose can be administered to animals, or, alternatively, two or more inoculations can take place with intervals of from about two to about ten weeks. Boosting regimens can be required, and the dosage regimen can be adjusted to provide optimal immunization. Those skilled in the art can readily determine the optimal administration regimen. When more than one dose is used, it is not necessarily the case that the first and second doses are administered to the same location in the animal.

Effective Immunogenic compositions can be administered directly into the bloodstream, into muscle, or into an internal organ. Suitable means for parenteral administration include intravenous, intra-arterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which can contain excipients such as salts, carbohydrates and buffering agents (preferably to a pH of from about 3 to about 9, or from about 4 to about 8, or from about 5 to about 7.5, or from about 6 to about 7.5, or about 7 to about 7.5), but for some applications, they can be more suitably formulated as a sterile non-aqueous solution, or as a dried form to be used in conjunction with a suitable vehicle such as sterile, pyrogen-free water. The preparation of parenteral formulations under sterile conditions, for example, by lyophilisation, can readily be accomplished using standard pharmaceutical techniques well known to those skilled in the art.

The solubility of compounds used in the preparation of parenteral solutions can be increased by the use of appropriate formulation techniques known to the skilled artisan, such as the incorporation of solubility-enhancing agents including buffers, salts, surfactants, liposomes, cyclodextrins, and the like.

Formulations for parenteral administration can be formulated to be immediate and/or modified release. Modified release formulations include delayed, sustained, pulsed, controlled, targeted and programmed release. Thus compounds of the invention can be formulated as a solid, semi-solid, or thixotropic liquid for administration as an implanted depot, providing modified release of the active compound. Examples of such formulations include drug-coated stents and poly(dl-lactic-coglycolic)acid (PLGA) microspheres.

Effective immunogenic compositions of the present invention can also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions; liposomes can also be used. Typical carriers include alcohol, water, mineral oil, liquid petrolatum, white petrolatum, glycerin, polyethylene glycol and propylene glycol. Penetration enhancers can be incorporated; see, for example, Finnin and Morgan, *J. Pharm Sci*, 88 (10):955-958 (1999). Other means of topical administration include delivery by electroporation, iontophoresis, phonophoresis, sonophoresis and microneedle or needle-free (e.g. Powderject™, Bioject™, etc.) injection. Formulations for topical administration can be designed to be immediate and/or modified release. Modified release formulations include delayed, sustained, pulsed, controlled, targeted and programmed release.

Effective immunogenic compositions can also be administered intranasally or by inhalation, typically in the form of a dry powder (either alone or as a mixture, for example, in a dry blend with lactose, or as a mixed component particle, for example, mixed with phospholipids, such as phosphatidylcholine), from a dry powder inhaler, or as an aerosol spray from a pressurized container, pump, spray, atomizer (preferably an atomizer using electrohydrodynamics) to produce a fine mist. It can also be administered via a nebulizer, with or without the use of a suitable propellant, such as 1,1,1,2-tetrafluoroethane or 1,1,1,2,3,3,3-heptafluoropropane. For intranasal use, the powder can comprise a bioadhesive agent, for example, chitosan or cyclodextrin. The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is generally micronized to a size suitable for delivery by inhalation (typically less than about 5 microns). This can be achieved by any appropriate comminuting method, such as spiral jet milling, fluid bed jet milling, supercritical fluid processing (to form nanoparticles), high pressure homogenization, or spray drying.

Capsules (made, for example, from gelatin or hydroxypropylmethylcellulose), blisters, and cartridges for use in an inhaler or insufflators, can be formulated to contain a powder mix of the compound of the invention. A suitable powder base could be lactose or starch, and a performance modifier could be l-leucine, mannitol, or magnesium stearate. The lactose can be anhydrous, or in the form of the monohydrate. Other suitable excipients include dextran, glucose, maltose, sorbitol, xylitol, fructose, sucrose and trehalose.

A suitable solution formulation for use in an atomizer, using electrohydrodynamics to produce a fine mist, can contain from about 1 µg to about 20 mg of the compound of the invention per actuation, and the actuation volume can vary from about 1 µl to about 100 µl. In another embodiment, the amount of compound per actuation can range from about 100 µg to about 15 mg, or from about 500 µg to about 10 mg, or from about 1 mg to about 10 mg, or from about 2.5 µg to about 5 mg. In another embodiment, the actuation volume can range from about 5 µl to about 75 µl, or from about 10 µl to about 50 µl, or from about 15 µl to about 25 µl. A typical formulation can comprise the compound of the invention, propylene glycol, sterile water, ethanol and sodium chloride. Alternative solvents which can be used instead of propylene glycol include glycerol and polyethylene glycol.

Formulations for inhaled/intranasal administration can be formulated to be immediate and/or modified release using, for example, PLGA. Modified release formulations include delayed, sustained, pulsed, controlled, targeted and programmed release.

In the case of dry powder inhalers and aerosols, the dosage unit is generally determined by means of a valve which delivers a metered amount. Units in accordance with the invention are typically arranged to administer a metered dose or "puff" containing from about 10 ng to about 100 µg of the compound of the invention. In another embodiment, the amount of compound administered in a metered dose is from about 50 ng to about 75 µg, or from about 100 ng to about 50 µg, or from about 500 ng to about 25 µg, or from about 750 ng to about 10 µg, or from about 1 µg to about 5 µg. The overall daily dose will typically be in the range from about 1 µg to about 100 mg, which can be administered in a single dose or, more usually, as divided doses throughout the day. In another embodiment, the overall daily dose can range from about 50 µg to about 75 mg, or from about 100 µg to about 50 mg, or from about 500 µg to about 25 mg, or from about 750 µg to about 10 mg, or from about 1 mg to about 5 mg.

Effective immunogenic compositions of the present invention can also be administered orally or perorally, that is, into a subject's body through or by way of the mouth, and involves swallowing or transport through the oral mucosa (e.g., sublingual or buccal absorption, or both). Suitable flavors, such as menthol and levomenthol, or sweeteners, such as saccharin or saccharin sodium, can be added to those formulations of the invention intended for oral or peroral administration.

Effective immunogenic compositions of the present invention can be administered rectally or vaginally, for example, in the form of a suppository, pessary, or enema. Cocoa butter is a traditional suppository base, but various alternatives can be used as appropriate. Formulations for rectal/vaginal administration can be formulated to be immediate and/or modified release. Modified release formulations include delayed, sustained, pulsed, controlled, targeted and programmed release.

Effective immunogenic compositions of the present invention can also be administered directly to the eye or ear, typically in the form of drops of a micronized suspension, or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, can be incorporated together with a preservative, such as benzalkonium chloride. Such formulations can also be delivered by iontophoresis. Formulations for ocular/aural administration can be formulated to be immediate and/or modified release. Modified release formulations include delayed, sustained, pulsed, controlled, targeted and programmed release.

The immunogenic compositions of the present invention, are not limited by the selection of the conventional, physiologically-acceptable carriers, adjuvants, or other ingredients useful in pharmaceutical preparations of the types described above. The preparation of these pharmaceutically acceptable compositions, from the above-described components, having appropriate pH isotonicity, stability and other conventional characteristics, is within the skill of the art.

In general, selection of the appropriate "effective amount" or dosage for the components of the immunogenic compositions of the present invention will also be based upon the identity of the antigen in the immunogenic composition(s) employed, as well as the physical condition of the subject, most especially including the general health, age and weight of the immunized subject. The method and routes of administration, and the presence of additional components in the immunogenic compositions, may also affect the dosages and amounts of the compositions. Such selection, and upward or downward adjustment of the effective dose, is within the skill of the art. The amount of composition required to induce an immune response, preferably a protective response, or produce an exogenous effect in the subject without significant adverse side effects, can vary, depending upon these factors. Suitable doses are readily determined by persons skilled in the art.

Similarly, the order of immunogenic composition administration and the time periods between individual administrations, if more than one is necessary, may be selected by one of skill in the art based upon the physical characteristics and precise responses of the host to the application of the method. Preferably, the effective immunogenic composition of the present invention can be administered to a bovine animal that is 1 day to 3 weeks of age. More preferably, it can be administered to a bovine animal that is 1-2 weeks of age. It should be noted, again, based on the particular exposure risks present on any particular breeding or ranching operation, that a further preferred aspect of the invention includes vaccinating calves with the modified live (attenuated) vaccines of the present invention at any age, such as 0 to 3 weeks of age, 0 to 2 months of age, and 0 to 6 months of age. For an effective immunogenic composition comprising a modified-live *M. bovis*, only a single administration is generally necessary, and that administration can be carried out in a bovine animal at an age as described above. However, it can be administered more than once, for example, subsequent doses being given at 2-4 week intervals following the first vaccination. However, depending on various factors including the prevalence of disease in a herd, and the presence of particularly pathogenic circulating field strains, it may be appropriate to administer one or multiple doses of the live vaccine of the present invention over time to a given animal, irrespective of the age of the vaccinated animal. Thus older animals may also be vaccinated, and repetitively vaccined according to the practice of the present invention, which is particularly important in respect of female bovines both before the onset of, and during pregnancy. Thus in one further preferred example, a female bovine is vaccinated between 2 and 4 months prior to the start of pregnancy, even if the cow had been previously vaccinated, and the calf is vaccinated soon after birth. Under some circumstances it may be additionally appropriate to vaccinate the mother cow during pregnancy.

For other types of *M. bovis* vaccines (e.g. killed or subunit), the initial administration of the composition can be at an age as outlined above, with subsequent administrations 2-4 weeks following the previous dose.

Kits

Inasmuch as it may be desirable to administer an immunogenic composition individually or in combination with additional compounds, for example, for the purpose of treating a particular disease or condition, it is within the scope of the present invention that an immunogenic composition can conveniently be included in, or combined in, the form of a kit suitable for administration or co-administration of the compositions. Kits of the present invention can comprise one or more separate pharmaceutical compositions, at least one of which is an immunogenic composition in accordance with the present invention, and a means for separately retaining said compositions, such as containers, a divided bottle, or a divided foil packet. An example of such a kit is a syringe and needle, and the like. A kit of the present invention is particularly suitable for administering different dosage forms, for example, oral or parenteral, for administering the separate compositions at different dosage intervals, or for titrating the separate compositions against one another. To assist one administering a composition of the present invention, the kit typically comprises directions for administration.

Another kit of the present invention can comprise one or more reagents useful for the detection of *M. bovis*. The kit can include reagents for analyzing a sample for the presence of whole *M. bovis*, or *M. bovis* polypeptides, epitopes or polynucleotide sequences. In certain embodiments, the kits can include a set of printed instructions or a label indicating that the kit is useful for the detection of animals infected with M. bovis.

Antibody, Antibodies

Antibodies can either be monoclonal, polyclonal, or recombinant. The antibodies can be prepared against the immunogen or a portion thereof. For example, a synthetic peptide based on the amino acid sequence of the immunogen, or prepared recombinantly by cloning techniques, or the natural gene product and/or portions thereof, can be isolated and used as the immunogen. Immunogens can be used to produce antibodies by standard antibody production technology well known to those skilled in the art, such as described generally in Harlow and Lane, "Antibodies: A Laboratory Manual", Cold Spring Harbor Laboratory, Cold Spring Harbor, N.Y., (1988), and Borrebaeck, "Antibody Engineering—A Practical Guide", W.H. Freeman and Co. (1992). Antibody fragments can also be prepared from the antibodies, and include Fab, F(ab')$_2$, and Fv, by methods known to those skilled in the art.

In one embodiment of the present invention the antibody of the invention further provides an intact immunoglobulin capable of specific binding to a target, such as a carbohydrate, polynucleotide, lipid, polypeptide, etc., through at least one antigen recognition site located in the variable region of the immunoglobulin molecule. An intact antibody has two light and two heavy chains. Thus a single isolated intact antibody may be a polyclonal antibody, a monoclonal antibody, a synthetic antibody, a recombinant antibody, a chimeric antibody, or a heterochimeric antibody.

In the production of antibodies, screening for the desired antibody can be accomplished by standard methods in immunology known in the art. Techniques not specifically described are generally followed as in Stites, et al. (eds), "Basic and Clinical Immunology" (8th Edition), Appleton and Lange, Norwalk, Conn. (1994), and Mishell and Shiigi (eds), "Selected Methods in Cellular Immunology", W.H. Freeman and Co., New York (1980). In general, ELISAs and Western blotting are the preferred types of immunoassays; both assays are well known to those skilled in the art. Both polyclonal and monoclonal antibodies can be used in the assays. The antibody can be bound to a solid support substrate, or conjugated with a detectable moiety, or be both bound and conjugated as is well known in the art. (For a general discussion of conjugation of fluorescent or enzymatic moieties, see Johnstone and Thorpe, "Immunochemistry in Practice", Blackwell Scientific Publications, Oxford (1982).) The binding of antibodies to a solid support substrate is also well known in the art. (For a general discussion, see Harlow and Lane (1988), as well as Borrebaeck (1992).) The detectable moieties contemplated for use in the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, $^{14}$C and iodination.

Recombinant Techniques

In yet other embodiments of the invention, the immunogenic composition may comprise a recombinant vaccine. Such recombinant vaccines would generally comprise a vector and a heterologous insert comprising a M. bovis antigen. Suitable M. bovis antigens may include membrane and membrane-associated proteins, including but not limited to the variable surface proteins (Vsps); cytadhesins; lipoproteins, for example P48 and P68; as well as potentially other hypothetical proteins that remain to be investigated and characterized.

The insert may optionally comprise a heterologous promoter, such as, for example, synthetic promoters known in the art. Alternatively, the promoters of the host vector may exert transcriptional control over the expression of the inserts. Suitable non-limiting examples of promoters (which may be native or heterologous, depending on the choice of the vector) are H6 vaccinia promoter, I3L vaccinia promoter, 42K poxviral promoter, 7.5K vaccinia promoter, and Pi vaccinia promoter.

Suitable vectors have been described elsewhere in this application. In some embodiments, the vectors may be viral vectors, including, without limitations, vaccinia and pox viral vectors, such as parapox, racoonpox, swinepox, and different avipox vectors (e.g., canarypox and fowlpox strains). Currently contemplated viral strains include D1701, ALVAC, TROVAC, NYVAC strains. Generally, sequences that are non-essential for the viral host are suitable insertions sites for the inserts of the instant invention. The strains recited above are well-characterized in the art and some insertions sites in these vectors are well known. See, e.g., U.S. Pat. Nos. 5,174,993; 5,505,941 5,766,599 5,756,103, 7,638,134, 6,365,393.

There are several known methods or techniques that can be used to clone and express the nucleotide sequences of the present invention. For example, the sequences can be isolated as restriction fragments and cloned into cloning and/or expression vectors. The sequences can also be PCR amplified and cloned into cloning and/or expression vectors, or they can be cloned by a combination of these two methods. Standard molecular biology techniques known in the art, and not specifically described, can be generally followed as described in Sambrook et al., *Molecular Cloning: A Laboratory Manual*, Cold Spring Harbor Laboratory Press, New York (1989); Ausubel et al., *Current Protocols in Molecular Biology*, John Wiley and Sons, Baltimore, Md. (1989); Perbal, *A Practical Guide to Molecular Cloning*, John Wiley & Sons, New York (1988); Watson et al., *Recombinant DNA*, Scientific American Books, New York; Birren et al (eds) *Genome Analysis: A Laboratory Manual Series*, Vols. 1-4 Cold Spring Harbor Laboratory Press, New York (1998); and methodology set forth in U.S. Pat. Nos. 4,666,828; 4,683,202; 4,801,531; 5,192,659 and 5,272,057. Polymerase chain reaction (PCR) is carried out generally as described in *PCR Protocols: A Guide to Methods and Applications*, Academic Press, San Diego, Calif. (1990).

The present invention encompasses the use of prokaryotic and eukaryotic expression systems, including vectors and host cells, which may be used to express both truncated and full-length forms of the recombinant polypeptides expressed by the nucleotide sequences of the present invention. A variety of host-expression vector systems may be utilized to express the polypeptides of the present invention. Such host-expression systems also represent vehicles by which the coding sequences of interest may be cloned and subsequently purified. The present invention further provides for host cells which may, when transformed or transfected with the appropriate vector or nucleotide sequence, express the encoded polypeptide gene product of the invention. Such host cells include, but are not limited to, microorganisms such as bacteria (e.g., E. coli, B. subtilis) transformed with recombinant bacteriophage DNA, plasmid DNA or cosmid DNA expression vectors containing coding sequences; yeast (e.g., Saccharomyces, Pichia) transformed with recombinant yeast expression vectors containing the gene product coding sequences; insect cell systems infected with recombinant virus expression vectors (e.g., baculovirus) containing the coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

Generally, the vectors of the invention can be derived from, but not limited to, bacterial plasmids, from bacteriophage, from yeast episomes, from yeast chromosomal elements, from viruses (e.g., as described above), from mammalian chromosomes, and from combinations thereof, such as those derived from plasmid and bacteriophage genetic elements including, but not limited to, cosmids and phagemids.

Vectors of the present invention can be used for the expression of M. bovis polypeptides. Generally, the vectors of the invention include cis-acting regulatory regions operably linked to the polynucleotide that encodes the polypeptides to be expressed. The regulatory regions may be constitutive or inducible. Appropriate trans-acting factors are supplied by the host by an in vitro translation system, by a complementing vector, or by the vector itself upon introduction into the host.

The vectors of the invention can include any elements typically included in an expression or display vector, including, but not limited to, origin of replication sequences, one or more promoters, antibiotic resistance genes, leader or signal peptide sequences, various tag sequences, stuffer sequences that may encode a gene whose polypeptide confers antibiotic resistance, restriction sites, ribosome binding sites, translational enhancers (sequences capable of forming stem loop structures for mRNA stability post-transcription), sequences that encode amino acids lacking a stop codon, and sequences that encode a bacterial coat protein.

The present invention is further illustrated by, but by no means limited to, the following examples.

Example 1. Generation and Isolation of a *Mycoplasma bovis* Mutant

*Mycoplasma bovis*, isolated from the joint of a bovine (Millmerran, Queensland; 1999), was passaged twice in *Mycoplasma bovis* ("*Bovis*") broth (PPLO; yeast extract; phenol red; heat-inactivated, γ-irradiated swine serum), filter-cloned 4× on *Bovis* agar, and then further passaged in broth. A culture of the strain (10 ml) was prepared, and incubated at the appropriate temperature for 24 hrs. After that time, the culture was harvested by centrifugation at 13,000 g for 10 minutes at 4'C. The resultant pellet was washed 3× with 1 ml of phosphate-buffered saline (PBS). The final pellet was resuspended in 1 ml PBS, and split between two 1.5 ml eppendorf tubes. The strain (designated 3683) was mutagenized using the chemical, methylnitronitrosoguanidine (NTG). Temperature-sensitive mutants of *M. bovis* were generated and selected according to the protocol described originally in Nonomura and Imada (Avian Dis. 26(4):763-775; 1982). Following mutagenesis and phenotypic selection, filter cloning and passaging in *Bovis* broth was carried out.

A calf was intranasally inoculated with a purified clone of a temperature-sensitive mutant designated 3683 #22/3/12. *M. bovis* isolate N2805-1 was subsequently obtained from a swab collected from the nasopharynx of that specific calf, according to the following procedure: *Mycoplasma* broth containing nasal swab material collected 28 days after infection was plated on PPLO agar plates, which were then incubated at 38.3° C. in a 5% $CO_2$ atmosphere. An individual colony was picked and transferred to PPLO broth, and incubated at 38.3° C. in a 5% $CO_2$ atmosphere for 48 hours. The broth culture was then passed through a sterile 0.45 micron filter, diluted in saline, and plated on PPLO agar, in order to obtain individual colonies. A total of 8 passages were performed, alternating between broth and plates, with the broth phase being filtered prior to plating, to obtain individual colonies. This resulted in a total of 3 filter/cloning steps. The final broth passage was divided into 2 aliquots, which were then stored at −80° C. A frozen aliquot was subsequently thawed, and used to inoculate 60 ml of PPLO broth. After 48 hours of incubation at 38.3° C. in 5% $CO_2$, the culture was dispensed into 1.25 ml aliquots, and frozen at −80° C., to serve as working stock. One vial of stock was thawed and used to inoculate 200 ml of PPLO broth, which was then incubated for 24 hours at 37° C. in 5% $CO_2$. The culture was then dispensed into 1.25 ml aliquots and frozen at −80° C. All subsequent work was performed using this material ("passage 10").

Because the strain used to vaccinate the calf from which N2805-1 was eventually recovered was temperature-sensitive, the phenotypic characteristics of N2805-1 at both the restrictive (38.3° C.) and permissive (33° C.) temperatures were evaluated. Growth of N2805-1 at the restrictive temperature was at least as good as, if not better than, growth at the permissive temperature (Table 1), indicating that N2805-1 no longer exhibited a temperature-sensitive phenotype.

TABLE 1

| Elapsed time (hrs) | 33° C. | 38.3° C. |
|---|---|---|
| 0 | 7.67E+05 | 5.67E+05 |
| 15.5 | 2.33E+06 | 8.67E+06 |
| 18.5 | 2.00E+07 | 1.77E+07 |
| 21.5 | 4.80E+07 | 3.67E+07 |
| 24 | 4.33E+07 | 5.43E+07 |
| 39.5 | 1.83E+08 | 1.20E+08 |

Figure 1:
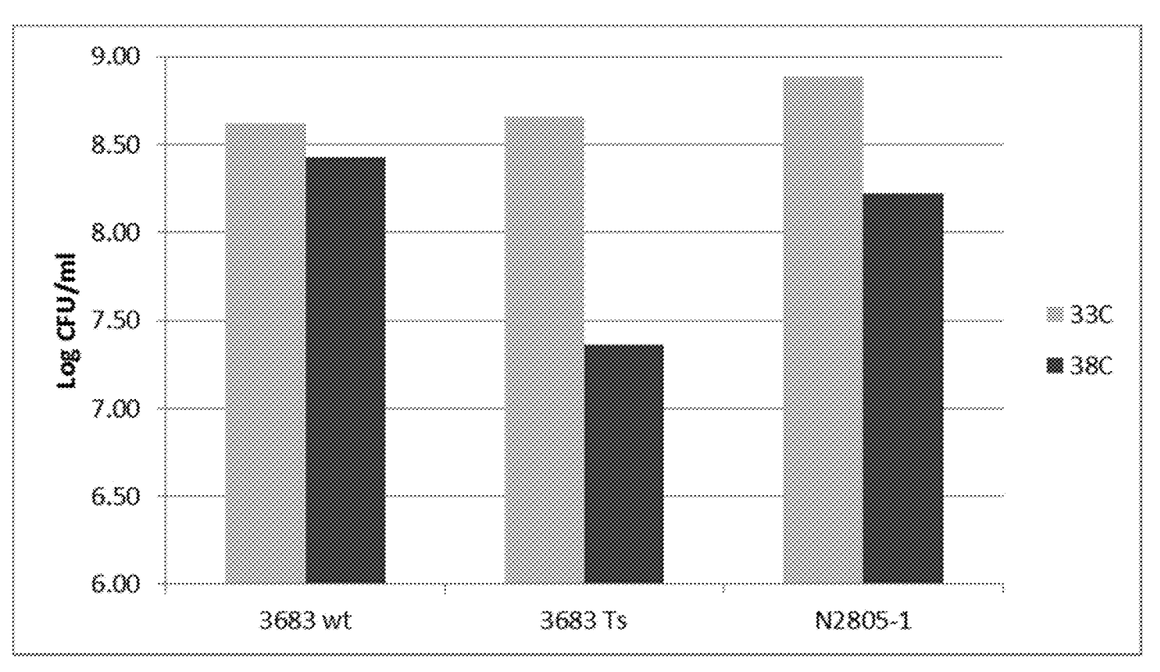
FIG. 1 provides a comparison of the growth rates at 33° C. and 38° C. of wild-type *Mycoplasma bovis* strain 3683, *M. bovis* temperature-sensitive mutant #22/3/12, and *M. bovis* mutant N2805-1.

In a separate study, the growth rate of N2805-1 was compared to that of the temperature-sensitive mutant, 3683 #22/3/12, and the parent strain (3683) from which it was derived. PPLO broth containing 10% porcine serum was inoculated with 1% (v/v) of thawed frozen stock culture of each strain. Duplicate broth cultures were prepared, and one was incubated at 33° C., and the other at 38° C., both with 5% $CO_2$. At 42 hours post-incubation, a 0.1 ml aliquot was removed from each culture, and CFU/ml was determined by serial dilution and plate count on PPLO agar. The plates were incubated at the same temperature as the corresponding broth culture for 5-7 days with 5% $CO_2$. The results in FIG. 1 demonstrate that at 42 hrs post-incubation, N2805-1 was no longer as temperature-sensitive as 3683 #22/3/12.

To characterize N2805-1 genotypically, the entire genome was sequenced, and compared to that of the parental wild-type (WT, premutagenized) strain 3683, from which it was derived. The result of that endeavor was that 12 different single nucleotide differences (single nucleotide polymorphisms, or SNPs) were identified between the 3683 *M. bovis* strains and derived N2805-1 strains. To date, 5 of those 12 SNPs have been confirmed by PCR. Exemplary changes in both the nucleotide and amino acid sequence of those 5 SNPs are shown in Table 2 (going from strain 3683 to isolate N2805-1).

TABLE 2

| SNP # | Description | Nucleotide Sequence in 3683 | Nucleotide Sequence in N2805-1 | Resulting Amino acid Change |
|---|---|---|---|---|
| 3 | a Nitroreductase | CAG | AAG | Glu > Lys |
| 6 | a Histidine acid phosphatase | GAT | AAT | Asp > Asn |
| 8 | a Excinuclease ABC subunit B | GCC | GTC | Ala > Val |
| 9 | a DNA polymerase III subunit beta | AGC | AAC | Ser > Asn |
| 10 | a ATP synthase F1 subunit delta | CTT | TTT | Leu > Phe |

Example 2. Efficacy of a Modified-Live *Mycoplasma bovis* Vaccine Strain Against a Virulent *Mycoplasma bovis* Heterologous Challenge Clinically healthy, colostrum-deprived (CD) calves were enrolled in the study. All calves were serologically negative (≤1:1600 titer) for *M. bovis* antibody by ELISA, and were PCR negative for *M. bovis* in nasal swabs collected before Day 0.

All calves also were BVDV persistent infection negative in ear notch tests. Animals were housed in separate rooms by treatment group, in individual pens, during the vaccination phase of this study. Treatment groups were co-mingled in four challenge rooms, and housed by block during the challenge phase. Any adverse events which occurred in calves during the course of the study were recorded.

On Study Day 0 (SD 0), 1-2 week old animals were intranasally administered (one nostril) one of the following vaccines (Table 3): T01, saline; T02, *M. bovis* vaccine strain N2805-1; T03; a reference experimental *M. bovis* vaccine (live-attenuated); T04, temperature-sensitive, earlier passage of *M. bovis* vaccine strain N2805-1. On SD 29-SD 31, all animals were challenged by aerosol with *M. bovis* Kansas strain 110LA-11-10. Calves were challenged using a small face mask (canine anesthetic mask) connected to a nebulizer, via a chamber which contained the aerosolized *M. bovis* challenge. Four nebulizers were connected to each chamber, which was in turn connected, by individual tubes, to four calves. Animals were subsequently necropsied on SD 56;

samples/tissues collected included: lung tissue, for PCR; lung swabs, 1 for isolation of *M. bovis*, and 1 for other bacteria; tonsil tissue; tracheobronchial lymph nodes; and lung lesion tissue.

TABLE 3

| Treatment Group | N | Target Vaccine Route and Dose (CFU/2 mL dose) | Target Challenge Dose and Exposure | Target Necropsy Day |
|---|---|---|---|---|
| T01 | 16 | IN, $1 \times 10^9$/calf | Aerosol on days 29, 30, 31 approximately $1 \times 10^8$ (1X culture) 30 min/calf | 56 |
| T02 | 16 | IN, $1 \times 10^9$/calf | | |
| T03 | 16 | IN, $1 \times 10^9$/calf | | |
| T04 | 16 | IN, $1 \times 10^9$/calf | | |

Results. The back transformed least square means (BTLSM) lung lesion scores (LLS) results are listed in Table 4. The vaccine administered to treatment groups T02, T03 and T04 induced a significant reduction in lung lesions compared to T01, saline controls (0%, 1%, and 1%, versus 17%, respectively).

TABLE 4

| Treatment Number | Number of Animals | Back[1] Transform LS mean | Standard Error % Lung with Lesions | Lower 90% Confidence Limit of Mean | Upper 90% Confidence Limit of Mean | Range % Lung with Lesions |
|---|---|---|---|---|---|---|
| T01 | 16 | 17$^c$ | 5 | 10 | 26 | 0 to 46 |
| T02 | 16 | 0$^a$ | 0 | 0 | 1 | 0 to 7 |
| T03 | 15 | 1$^b$ | 1 | 0 | 4 | 0 to 18 |
| T04 | 15 | 1$^{ab}$ | 1 | 0 | 4 | 0 to 59 |

[1]Treatment groups with the same letter are not significantly different at alpha = .10

Mean duration of pyrexia (>103.1° F.) is indicated in Table 5. All three vaccinated treatment groups had significantly fewer days of pyrexia when compared to controls.

TABLE 5

| Treatment number | Estimate[1] | lower 90% CI | upper 90% CI |
|---|---|---|---|
| T01 | 3.6$^b$ | 1.7 | 6.8 |
| T02 | 0.9$^a$ | 0.1 | 2.2 |
| T03 | 1.4$^a$ | 0.4 | 3.2 |
| T04 | 1.1$^a$ | 0.2 | 2.5 |

[1]Different superscripts within a column represent significant differences between groups Following challenge, the T01 group had a duration of clinical disease associated with *M. bovis* respiratory disease that averaged 4.7 days. This is contrasted with 0.7, 1.2 and 2.5 days respectively for the T02, T03 and T04 groups (Table 6). The T02 and T03 calves had a significant reduction in the mean duration of at least one clinical sign compared to T01 calves (P<0.0009 and P<0.0265).

The T02, T03 and T04 groups were protected from *M. bovis*-induced disease, as fewer animals exhibited clinical signs of cough, lameness and respiratory effort, and for a shorter duration of time compared with the T01 group. No animals in any group exhibited nasal discharge. Vaccinates did have droopy ear/head tilt slightly more often than the T01 group (Table 7).

TABLE 6

| Treatment number | Estimate[1] | lower 95% CI | upper 95% CI |
|---|---|---|---|
| T01 | 4.7[a] | 2.3 | 9.1 |
| T02 | 0.7[b] | 0.1 | 1.5 |
| T03 | 1.2[b] | 0.2 | 2.9 |
| T04 | 2.5[a] | 0.9 | 5.2 |

[1]Different superscripts within a column represent significant differences between groups

TABLE 7

| Ever | T01 | | T02 | | T03 | | T04 | |
|---|---|---|---|---|---|---|---|---|
| Present? | (%) | N(1) | (%) | N(1) | (%) | N(1) | (%) | N(1) |
| Cough | 56.3 | 16 | 18.8 | 16 | 26.7 | 15 | 46.7 | 15 |
| Lameness | 6.3 | 16 | 0.0 | 16 | 0.0 | 15 | 0.0 | 15 |
| Nasal Discharge | 0.0 | 16 | 0.0 | 16 | 0.0 | 15 | 0.0 | 15 |
| Respiratory Effort | 68.8 | 16 | 12.5 | 16 | 20.0 | 15 | 20.0 | 15 |
| Droopy Ear/ Head Tilt | 6.3 | 16 | 12.5 | 16 | 13.3 | 15 | 20.0 | 15 |

Nasal swabs were collected and tested by PCR for *M. bovis* weekly throughout the study. Detection by PCR peaked from day 7 to day 21 for the vaccinate groups. The T01 controls remained PCR negative during the vaccination phase. 100% of the T02 and T04 calves, and 93.3% of T03 calves were PCR positive during the study (Table 8).

TABLE 8

| Treatment No. | N | Day −1 | Day 7 | Day 14 | Day 21 | Day 27 | Day 36 | Day 43 | Day 55 | Ever Positive for Mycoplasma |
|---|---|---|---|---|---|---|---|---|---|---|
| T01 | 16 | 0.0% | 0.0% | 0.0% | 0.0% | 0.0% | 50.0% | 25.0% | 0.0% | 56.3% |
| T02 | 16 | 0.0% | 75.0% | 56.3% | 87.5% | 43.8% | 81.3% | 0.0% | 12.5% | 100.0% |
| T03 | 15 | 0.0% | 86.7% | 66.7% | 86.7% | 46.7% | 60.0% | 20.0% | 0.0% | 93.3% |
| T04 | 15 | 0.0% | 75.0% | 13.3% | 20.0% | 73.3% | 73.3% | 0.0% | 6.7 | 100.0% |

All animals were sero-negative for *M. bovis* (ELISA titers of ≤1:1600, or Geometric Mean ≤800) prior to the start of the study. Sero-conversion was detected at day 7 for T02 and T04 calves, and day 14 for the T03 group. Titer means were low across all groups until after challenge (Table 9).

The mucosal IgA antibody response to vaccination and challenge was monitored in nasal secretions using a *M. bovis*-specific IgA ELISA. A cut-off value of >1:50 was used to define a positive response. IgA antibody titers were induced by vaccination, and generally increased with study progression. IgA titers were higher for T02, T03 and T04 calves than T01 animals from day 7 through day 55. The peak response was day 43 for T01 and T02 groups, and day 55 for T03 and T04 groups (Table 10).

TABLE 9

| | Day −1 | | Day 7 | | Day 14 | | Day 21 | | Day 27 |
|---|---|---|---|---|---|---|---|---|---|
| Trt. | Geometric Mean | Range | Geometric Mean | Range | Geometric Mean | Range | Geometric Mean | Range | Geometric Mean |
| T01 | 800 | 800-800 | 800 | 800-800 | 800 | 800-800 | 800 | 800-800 | 800 |
| T02 | 800 | 800-800 | 911 | 800-3200 | 872 | 800-3200 | 911 | 800-1600 | 911 |
| T03 | 800 | 800-800 | 800 | 800-800 | 1038 | 800-12800 | 1132 | 800-6400 | 1346 |
| T04 | 800 | 800-800 | 872 | 800-1600 | 838 | 800-1600 | 1056 | 800-3200 | 962 |

| | | Day 36 | | Day 43 | | Day 55 | |
|---|---|---|---|---|---|---|---|
| Trt. | Day 27 Range | Geometric Mean | Range | Geometric Mean | Range | Geometric Mean | Range |
| T01 | 800-800 | 911 | 800-1600 | 2810 | 800-12800 | 17689 | 3200-51200 |
| T02 | 800-3200 | 3200 | 800-6400 | 9871 | 1600-25600 | 8668 | 3200-51200 |
| T03 | 800-12800 | 4223 | 800-12800 | 14018 | 1600-102400 | 11145 | 800-102400 |
| T04 | 800-3200 | 2786 | 800-6400 | 6704 | 800-102400 | 8445 | 1600-102400 |

TABLE 10

| Trt. | Day -1 Geometric Mean | Range | Day 7 Geometric Mean | Range | Day 14 Geometric Mean | Range | Day 21 Geometric Mean | Range | Day 27 Geometric Mean |
|---|---|---|---|---|---|---|---|---|---|
| T01 | 1 | 1-2 | 3 | 1-50 | 5 | 1-10 | 9 | 2-50 | 13 |
| T02 | 1 | 1-2 | 4 | 1-10 | 113 | 10-6250 | 152 | 50-6250 | 185 |
| T03 | 2 | 1-10 | 6 | 2-50 | 92 | 10-250 | 278 | 50-6250 | 205 |
| T04 | 1 | 1-2 | 6 | 1-50 | 69 | 10-250 | 132 | 50-250 | 226 |

| Trt. | Day 27 Range | Day 36 BTLSM | Range | Day 43 BTLSM | Range | Day 55 BTLSM | Range |
|---|---|---|---|---|---|---|---|
| T01 | 1-50 | 28 | 10-250 | 186 | 50-1250 | 234 | 50-1250 |
| T02 | 50-1250 | 251 | 50-1250 | 458 | 50-6250 | 506 | 250-6250 |
| T03 | 50-1250 | 227 | 50-1250 | 1018 | 250-31250 | 914 | 250-6250 |
| T04 | 50-6250 | 249 | 250-250 | 729 | 50-6250 | 588 | 250-6250 |

Lung, tonsil, and tracheobronchial lymph node samples were tested by PCR for *M. bovis**. (* *Mycoplasma agalactiae* can also be amplified in this PCR assay) *M. bovis* recovery was less frequent in all three vaccinated treatment groups in lung and lymph node tissue samples, compared to controls. Recovery from tonsils was high for all treatment groups (Table 11).

TABLE 11

| Treatment number | Lymph Node N | Lymph Node % | Tonsil N | Tonsil % | Lung Tissue N | Lung Tissue % |
|---|---|---|---|---|---|---|
| T01 | 12/16 | 75.0 | 16/16 | 100.0 | 16/16 | 100.0 |
| T02 | 7/16 | 43.8 | 16/16 | 100.0 | 9/16 | 56.3 |

TABLE 11-continued

| Treatment number | Lymph Node N | Lymph Node % | Tonsil N | Tonsil % | Lung Tissue N | Lung Tissue % |
|---|---|---|---|---|---|---|
| T03 | 9/15 | 60.0 | 15/15 | 100.0 | 8/15 | 53.3 |
| T04 | 6/15 | 40.0 | 12/15 | 80.0 | 9/15 | 60.0 |

* PCR data is from tissues collected at necropsy.

The rate of isolation of *M. bovis* from the lung swabs (day of necropsy) was lower in the T02, T03 and T04 calves, at 31.3%, 40.0% and 33.3%, compared to 87.5% for T01 controls. Lung swabs were negative for all other bacterial pathogens tested (Table 12).

TABLE 12

| Treatment number | *Mycoplasma bovis** % | *Mycoplasma bovis** N | *Histophilus somni* % | *Histophilus somni* N | *Mannheimia haemolytica* % | *Mannheimia haemolytica* N | *Pasteurella multocida* % | *Pasteurella multocida* N | *Beberstenia trehalosi* % | *Beberstenia trehalosi* N |
|---|---|---|---|---|---|---|---|---|---|---|
| T01 | 87.5 | 14 of 16 | 0 | 0 of 16 | 0 | 0 of 16 | 0 | 0 of 16 | 0 | 0 of 16 |
| T02 | 31.3 | 5 of 16 | 0 | 0 of 16 | 0 | 0 of 16 | 0 | 0 of 16 | 0 | 0 of 16 |
| T03 | 40.0 | 6 of 15 | 0 | 0 of 15 | 0 | 0 of 15 | 0 | 0 of 15 | 0 | 0 of 15 |
| T04 | 33.3 | 5 of 15 | 0 | 0 of 15 | 0 | 0 of 15 | 0 | 0 of 15 | 0 | 0 of 15 |

**Mycoplasma agalactiae* can also be amplified in this PCR assay.

The IFN gamma ELISPOT assay measured the induction of cell-mediated immunity after vaccination and challenge. IFN gamma spot-forming cells (SFCs) per million BTLSM (day −1 and day 42) and geometric means (day 7 and day 14) are listed in Table 13.

TABLE 13

| Treatment No | Day −1 BTLSM T02 | T03 | T04 | Day 7 Geometric Mean T02 | T03 | T04 | Day 14 Geometric Mean T02 | T03 | T04 | Day 42 BTLSM T02 | T03 | T04 |
|---|---|---|---|---|---|---|---|---|---|---|---|---|
| T01 | 491.8 | 300.9 | 456.6 | 556.8 | 231.5 | 243.1 | 219.8 | 258.8 | 246.5 | 1244 | 976.7 | 1101 |
| T02 | 273.8 | 160.4 | 210.4 | 797.6 | 350.8 | 599.3 | 195.8 | 214.7 | 163.4 | 1040.2 | 598.6 | 978.5 |
| T03 | 481.5 | 351.0 | 462.4 | 637.9 | 415.9 | 414.7 | 343.8 | 274.6 | 214.7 | 763.9 | 662.0 | 372.0 |
| T04 | 303.5 | 224.5 | 370.5 | 808.3 | 600.8 | 706.6 | 431.8 | 448.6 | 352.3 | 695.3 | 831.4 | 860.5 |

In conclusion, the N2805-1 vaccine candidate (T02) provided a significant reduction in lung lesion scores. Rectal temperatures and clinical signs of disease post-challenge were reduced in severity and duration by N2805-1. Serum antibody titers, IgA titers, and PCR and culture results also support the efficacy of this strain. Thus, the N2805-1 vaccine is a good candidate to evaluate for safety, and in further efficacy studies.

Example 3. Genomic Characterization of Temperature-Sensitive Mutant, 3863 22/3/12, and Non-Temperature Sensitive Mutant, N2805-1

In an effort to characterize the genomic differences between the *M. bovis* temperature-sensitive mutant, 3683 #22/3/12, and the non-temperature sensitive mutant, N2805-1, isolated from a calf which had been inoculated with 3683 #22/3/12, the genomes of both were sequenced using Illumina technology. DNA libraries were prepared, and barcoded samples were sequenced to obtain an average of 60× coverage of paired-end sequences per sample. Quality control of all reads was carried out, and failed and low quality reads were removed prior to mapping and single nucleotide polymorphism (SNP) analysis. Sequence reads were mapped to a reference genome (Hubei-1; Genbank accession number CP002513) using CLC Genomics workbench software (Qiagen; Redwood City, Calif.). The variant detection module from CLC Genomics workbench was used for SNP discovery. The identity and location of the SNPs are shown in Table 14. Between the two mutant strains, 56 SNPs were identified, 17 of which resulted in amino acid changes (including 2 which resulted in the introduction of a stop codon), 6 resulted in frameshift mutations, and 33 occurred in non-coding regions.

TABLE 14

| SNP Location* | Nucleotide Change# | Amino Acid Change# |
| --- | --- | --- |
| 115273 | T > C | (non-coding region) |
| 194478 | C > T | (non-coding region) |
| 194484 | T > C | (non-coding region) |
| 194525 | T > C | Thr > Ala |
| 194724 | G > A | (non-coding region) |
| 204966 | T > A | (non-coding region) |
| 207629 | A > G | (non-coding region) |
| 262327 | A > T | (non-coding region) |
| 271487 | C > T | Gly > Ser |
| 271661 | G > A | Gln > Stop |
| 271666 | G > — | Thr > frameshift |
| 272086 | T > A | Lys > Ile |
| 272133 | A > G | (non-coding region) |
| 309463 | C > — | Pro > frameshift |
| 310075 | A > T | Lys > Met |
| 310078 | T > A | Ile > Lys |
| 310086 | A > C | Asn > His |
| 310090 | A > C | Lys > Thr |
| 311988 | C > T | (non-coding region) |
| 334184 | A > — | (non-coding region) |
| 358013 | G > A | (non-coding region) |
| 365101 | T > C | (non-coding region) |
| 365188 | C > T | (non-coding region) |
| 397010 | T > — | Lys > frameshift |
| 397901 | T > — | (non-coding region) |
| 399129 | A > T | (non-coding region) |
| 410247 | A > T | (non-coding region) |
| 410253 | T > C | (non-coding region) |
| 410334 | G > A | (non-coding region) |
| 410514 | T > A | Arg > Ser |
| 410733 | T > C | (non-coding region) |
| 414666 | G > A | Gln > Stop |
| 453388 | A > G | (non-coding region) |

TABLE 14-continued

| SNP Location* | Nucleotide Change# | Amino Acid Change# |
| --- | --- | --- |
| 468457 | A > — | (non-coding region) |
| 502577 | A > G | Ile > Val |
| 502678 | C > T | (non-coding region) |
| 502963 | T > C | (non-coding region) |
| 543859 | G > T | (non-coding region) |
| 560986 | G > — | Gly > frameshift |
| 632309 | C > T | (non-coding region) |
| 632366 | A > G | (non-coding region) |
| 632612 | A > G | (non-coding region) |
| 633994 | T > — | Lys > frameshift |
| 686074 | T > C | (non-coding region) |
| 687874 | G > A | (non-coding region) |
| 687915 | C > A | Ala > Ser |
| 696348 | C > — | Gly > frameshift |
| 729874 | C > T | (non-coding region) |
| 730046 | C > T | Arg > Cys |
| 761587 | T > C | Thr > Ala |
| 761663 | G > A | (non-coding region) |
| 761810 | A > G | (non-coding region) |
| 761815 | T > C | Thr > Ala |
| 765176 | G > A | Ala > Thr |
| 765328 | T > C | (non-coding region) |
| 765403 | G > A | Met > Ile |

*Numbering of SNP locations is based on *Mycoplasma bovis* reference strain Hubei-1 (GenBank accession number CP002513).
Nucleotide and amino acid changes that occurred going from strain, 3863 #22/3/12, to strain N2805-1.

A *Mycoplasma bovis* strain from a bovine has been attenuated, as well as characterized. An isolate of said *M. bovis* strain was deposited with the American Type Culture Collection ("ATCC"), Manassas, Va., USA, on May 12, 2015, and has been assigned accession number, PTA-122167.

The invention claimed is:

1. An effective immunogenic composition comprising a *Mycoplasma bovis* strain, wherein said strain is deposited with the American Type Culture Collection under accession number PTA-122167, or wherein said strain is a progeny of *M bovis* strain PTA-122167 wherein said progeny of *M bovis* strain PTA-122167 is obtained by passaging strain PTA-122167.

2. The immunogenic composition of claim 1, wherein said *M. bovis* strain is inactivated.

3. The immunogenic composition of claim 2, wherein the composition additionally comprises an adjuvant.

4. The immunogenic composition of claim 2, further comprising at least one additional antigen.

5. The immunogenic composition of claim 4, wherein the additional antigen is selected from the group consisting of a virus, a bacterium, a fungus and a parasite.

6. The immunogenic composition of claim 1, wherein said composition is formulated for administration by a route selected from the group consisting of intramuscular, subcutaneous, intranasal, intratracheal, oral and aerosol.

7. A method for preventing disease caused by *Mycoplasma bovis* in a bovine animal, comprising administering to the animal an immunizing amount of the immunogenic composition of claim 1.

8. A method for preventing diseases caused by *Mycoplasma bovis* and another infectious agent of a bovine animal, comprising administering to the animal an immunizing amount of the immunogenic composition of claim 4.

9. A method for reducing at least one clinical sign of disease caused by *Mycoplasma bovis* in a bovine animal, comprising administering to the animal an immunizing amount of the immunogenic composition of claim 1.

10. The method according to claim 9, wherein said at least one clinical sign is selected form the group consisting of a lung lesions, pyrexia, cough, lameness, and difficulty breathing.

11. A method for preventing at least one clinical sign of diseases caused by *Mycoplasma bovis* and another infectious agent of a bovine animal, comprising administering to the animal an immunizing amount of the immunogenic composition of claim 4.

12. The method according to claim 11, wherein said at least one clinical sign of the disease caused by *M bovis* is selected form the group consisting of a lung lesions, pyrexia, cough, lameness, and difficulty breathing.

\* \* \* \* \*